(12) United States Patent
Leonard et al.

(10) Patent No.: US 8,536,243 B2
(45) Date of Patent: Sep. 17, 2013

(54) TWO-COMPONENT SYSTEM FOR BONE CEMENT

(75) Inventors: Alain Leonard, Caixon (FR); Cyril Sender, Toulouse (FR); Claudine Lavergne, Caixon (FR); Benoît Donazzon, Lanta (FR)

(73) Assignee: Teknimed SAS, Vic-en-Bigorre (FR)

( * ) Notice: Subject to any disclaimer, the term of this patent is extended or adjusted under 35 U.S.C. 154(b) by 198 days.

(21) Appl. No.: 12/766,530

(22) Filed: Apr. 23, 2010

(65) Prior Publication Data

US 2011/0237705 A1 Sep. 29, 2011

(30) Foreign Application Priority Data

Mar. 23, 2010 (FR) ..................................... 10 01137

(51) Int. Cl.
*A61F 2/28* (2006.01)
(52) U.S. Cl.
USPC ........... 523/117; 523/116; 525/387; 424/423; 623/16.11
(58) Field of Classification Search
USPC ................. 523/117, 116; 525/387; 424/423; 623/16.11
See application file for complete search history.

(56) References Cited

U.S. PATENT DOCUMENTS

| 4,963,151 A * | 10/1990 | Ducheyne et al. ......... 623/23.62 |
| 5,795,922 A * | 8/1998 | Demian et al. ................. 523/117 |
| 5,902,839 A * | 5/1999 | Lautenschlager et al. .... 523/115 |
| 7,259,210 B2 * | 8/2007 | Puckett et al. ................ 525/193 |
| 7,981,945 B2 * | 7/2011 | Shalaby et al. ............... 523/117 |
| 2007/0032567 A1 * | 2/2007 | Beyar et al. .................... 523/116 |

FOREIGN PATENT DOCUMENTS

| CA | 2682140 | 10/2008 |
| WO | WO 2007/015202 | 2/2007 |
| WO | WO 2010/005442 | 1/2010 |

OTHER PUBLICATIONS

Product Information of Degacryll M 546 by Evonik Industries, 1 page, Nov. 1, 2004.*

* cited by examiner

*Primary Examiner* — Tae H Yoon
(74) *Attorney, Agent, or Firm* — Young & Thompson

(57) ABSTRACT

The invention relates to a system for preparing a polymerized bone cement, including two components reacting with each other when they are mixed to form a solid polymer material. The first component may include a biocompatible acrylic polymer and an initiator capable of initiating a polymerization reaction. The second component may include a monomer capable of dissolving an acrylic polymer, a polymerization activator and a polymerization inhibitor, system in which the second component also includes a biocompatible acrylic polymer dissolved in said monomer, identical or different from the polymer of the first component with an average molar mass greater than 1,000,000 g/mol and a residual initiator content of less than 0.1% to form a gel with determined viscosity. Another object of the invention is a composition designed to constitute the second component of as system used to prepare such cement.

20 Claims, 2 Drawing Sheets

TWO-COMPONENT SYSTEM FOR BONE CEMENT

BACKGROUND OF THE INVENTION

1. Field of the Invention

This application claims the benefit of French Patent Application No. 10/01137, filed Mar. 23, 2010.

This invention relates to the field of implantable biomaterials known as bone cements and more specifically to the field of acrylic cements used for vertebroplasty and the sealing of prostheses.

It concerns a system for preparing a bone cement polymer comprising two components which react with each other when they are mixed to form a solid polymer material, one of which is provided in the form of a gel with high stability under normal storage conditions. Another aim of the invention is a composition intended for use in the preparation of such cement.

2. Description of the Related Art

Nowadays, bone cements are widely used in orthopedic surgery in the sealing of prostheses (hip, knee, shoulder), treatment of vertebral compression fractures, or as filling material for vertebroplasty. In particular, the techniques of vertebroplasty and kyphoplasty are used to restore vertebrae damaged by trauma or disease. It is thus possible to relieve back pain when analgesic treatments are ineffective.

These techniques are of great interest to patients because the pain relief rate is very high and fast. The literature reports a net decrease or disappearance of back pain in 80 to 90% of cases. There is also an obvious improvement in mobility and quality of life for patients treated within hours or days after surgery. In cases of vertebral bone tumors, vertebroplasty provides significant and rapid relief and allows patients to regain a standing position within 24 to 72 hours after surgery.

The technique of percutaneous vertebroplasty has been used for about 20 years and has become a growing success. It involves injecting cement based on polymethylmethacrylate (PMMA) into the vertebrae under fluoroscopic and/or tomographic control.

The majority of currently used cements are prepared from two-component systems that must be mixed just before its implementation to obtain an implantable material. The first component essentially consists of a prepolymer powder and the second component of a liquid monomer. The liquid monomer, typically methylmethacrylate (MMA) additionally contains a polymerization activator such as pyridylmethyltoluidine (DMTP), the role of which is to accelerate the chain reaction, and an inhibitor such as hydroquinone (HQ) which prevents spontaneous polymerization of the monomer. The prepolymer, typically consisting of poly(methylmethacrylate) (PMMA) is in the form of small spherical balls or beads. It contains in turn a polymerization initiator such as benzoyl peroxide (BPo). A radiopaque compound may be mixed with the powder to allow visualizing the cement during and after injection.

Upon the mixture of the two components, the initiator present in the powder phase reacts with the gas present in the liquid phase to create highly reactive chemical species (free radicals) that initiate the polymerization chain.

The mixture acquires a certain consistency, a given viscosity level, which differs depending on the cements and their preparation conditions and which will eventually evolve gradually to form a solid mass. For example, the sealing cements are, after mixing the powder and liquid components, either very watery (called "low viscosity") or very pasty (called "high viscosity"). It is the same for cements used in vertebroplasty or kyphoplasty.

The viscosity of cement immediately after mixing is now controlled by the partial dissolution of beads present in the first prepolymer component by the monomer liquid of the second component. It then increases the average molecular weight of prepolymer chains involved in expanding the polymerization reaction, which induces a gradual increase in viscosity. The process and the kinetics of polymerization of acrylic cements used in orthopedic surgery are well known to those skilled in the craft, as are the mechanical properties of cements obtained.

We know in particular that the monomer and the prepolymer must be made in such proportions that the reaction is as complete as possible. Indeed, if the monomer is in excess, an undesirable release phenomenon will occur, while if it is of insufficient quantity the un-dissolved prepolymer balls will give the cement a grainy appearance and make it fragile. Thus, for a cement vertebroplasty, it is recommended to follow a prepolymer and monomer ratio of about 1.5; this ratio may go up to about 3 for the sealing of prosthesis.

In practice, the surgeon will, based on data provided in the instructions for use of cement, therapeutic indications and his personal opinion, judge when the consistency of cement has reached a satisfactory level in order to begin implementation with minimal risk to the patient. Depending on the type of cement, one of two situations will arise.

If the cement is a low viscosity cement, the surgeon must wait until polymerization progresses in order to begin the implementation of cement. This dead time, which may last up to 15 minutes, is time lost. The risks associated with the implantation of "low viscosity" acrylic cement originate in particular the risk of a too-fluid concrete passing into the circulatory system. Taking into account this risk requires the practitioner to make an accurate, though largely empirical, assessment of the viscosity level achieved.

If, however, the cement is a high viscosity cement, the surgeon may begin the implantation of the completed mixture, but must operate using sophisticated, and therefore expensive, injection systems, In both cases, the viscosity of the mixture changes very quickly and the implementation must be conducted expeditiously once it has reached the desired level. The surgeon must operate in a very short period of time, usually several minutes, which is a significant additional burden for him and a risk to the patient.

To overcome these problems, using a low-viscosity type cement is proposed, one whose formulation is designed so that, immediately after mixing the components, the viscosity is at a level sufficient to begin its implementation. An adequately pasty consistency every time immediately after mixing would eliminate waiting time and reduce the risk of too-watery cement passing into the circulatory system, reducing uncertainty in addition to the subjective assessment of the practitioner. Similarly, a longer implementation time (over 10 minutes for example) would allow the surgeon to implant cements in a more controlled and mastered manner.

The solution proposed to address these requirements is based on the use of a two-component system, in which the second component is in the form of a viscous gel rather than in liquid form.

This gel is obtained by dissolving a certain amount of prepolymer beads in a liquid monomer. In doing so, the usual reagents are used, the first component including a polymerization initiator, and the second component including a polymerization reaction accelerator (activator) and a polymerization inhibitor. Consequently, the very low viscosity liquid phase containing the monomer of the current system with two components is replaced by a phase in the form of a gel that, after being mixed with the powder phase, gives the cement a higher viscosity level.

When mixing the second gel component with the first powder component, a cement paste is obtained, the consistency of which can be implemented without waiting time, which has the added advantage of a viscosity well calibrated to the initial time $t_0$, and not subjectively assessed after a longer or shorter period.

In practice, however, it was found that the second component had a reduced stability that prevented permanent storage or imposed refrigerated storage. Indeed, despite the presence of hydroquinone in the inhibitory component gel, it was observed that polymerization occurs after a certain period of time. This problem is well known since there are currently marketed products in the form of gels, which are either made from acrylic monomers like Bis-GMA, Bis-EMA, TEGDMA or UDMA (e.g. Cortoss™ cement from Orthovita), or from MMA and PMMA [Shim et al., Biomaterials, 2005], and all these acrylic gels must be stored and transported under refrigerated conditions, failing which they are usable only for a very short time, about a few months. Knowing that cements currently used in orthopedics have 3-year expiration periods in normal ambient temperature conditions, we understand that hospitals do not want to be forced to organize the cold storage of such medical devices, which would impose significant logistical constraints.

However, to date, no alternative solution to maintaining the cold has been proposed to allow storage of products at room temperature without any premature polymerization occurring.

SUMMARY OF THE INVENTION

The authors of this invention then hypothesized that a chemical factor not taken into account could affect the kinetics of the reaction in the long term. Following the studies conducted, it unexpectedly appeared that polymerization was induced by the presence in the second component of a small amount of initiator, and that the latter was contributed by the polymer.

Indeed, after verification, it appeared that a reagent such as BPo, found even residually in the polymer, was able to initiate polymerization when the polymer was in the presence of the monomer. However, residual BPo is commonly found in PMMA powders in commerce up to 0.08% by weight, and often more.

Although the role of initiators, including BPo, are well known to those skilled in the craft, the origin of the specific problem of solidifying acrylic gels has not yet been identified. For example, patent application EP2008/053640 describes a bone cement injection obtained by mixing a gel and a paste. The gel is obtained by dissolving acrylic polymers such as PMMA in a monomer such as MMA. The paste contains an acrylic polymer and BPo in the powder state, i.e. non-dissolving. The question of stability of the paste during storage was noted as a particularly significant advantage in insisting that the BPo powder does not interact with other ingredients and does not cause premature polymerization of the paste. Conversely, regarding the stability of the gel, the emphasis is on the logistical problems engendered by the stress of cold storage to ensure a long life and proper use under optimal conditions in the operating room. The presence of residual BPo in polymers is not implicated in the instability of frozen storage.

It appeared that it was possible, by judicious choice of a prepolymer with relatively high molecular weight, containing little initiator (or not containing any at all), to delay by several months, even years, the polymerization of the prepolymer in the monomer.

Thus, this invention aims to overcome the drawbacks of current cements in terms of handling and implantation, outlined above, by proposing a bone cement composed of two parts, one a gel of determined viscosity which is stable over time under normal conditions.

One objective of the invention is to provide bone cement with a pasty and well-defined consistency immediately after the mixing of components. This would eliminate waiting time for the practitioner, while also reducing risks associated with the manipulation of a too-watery cement passing into the circulatory system.

Another objective of the invention is to provide cement whose viscosity evolves more slowly than conventional cements, in order to have a longer implementation time, for example more than 10 minutes.

The combination of these two properties is particularly sought after. Indeed, as part of vertebroplasty or kyphoplasty techniques, the risk of extravertebral leaks causing serious complications (pulmonary embolism, cardiac arrest, etc.) would be greatly limited by the possibility of injecting without waiting a cement with suitable viscosity, and continue the operation progressively without worries about premature hardening in the injection system.

Another object of this invention is to provide a system for the preparation of a cement from two components with the properties mentioned above, not evolving during storage, so that these properties are preserved and characteristics of the cement obtained are guaranteed when the time comes for its preparation and implementation by the practitioner. This goal is crucial in the context of this invention, since a system whose stability is not ensured would not meet the previous objective of viscosity control.

Thus, this invention provides a system for preparing a bone cement polymer comprising two components, which react with each other when mixed to form a solid polymer material, The first component includes a biocompatible acrylic polymer and an initiator capable of initiating a polymerization reaction, and The second component includes a monomer capable of dissolving an acrylic polymer, a polymerization activator and a polymerization inhibitor, system in which the second component also includes a biocompatible polymer dissolved in said acrylic monomer, identical or different from the first polymer component having an average molecular weight greater than 1,000,000 g/mol and a residual initiator less than 0.1% to form a gel of determined viscosity.

To obtain a cement with a pasty, well-defined consistency immediately after mixing the components, this invention proposes the use of a second component containing a monomer in gel form, not in liquid form as in prior conventional techniques. Dissolution in a monomer, initially liquid, of a certain amount of polymer chosen according to the invention achieves an increase in the viscosity of the mixture, which is manifested by gelation of the second component of the system at a determined level and stable in the long term.

The polymers and monomers used for this invention are obviously all biocompatible, given the intended application. This characteristic will not be repeated throughout the following description.

Similarly, the acrylic polymers used in the composition of the two components are intended to participate in subsequent polymerization reactions to form the bone cement. This is why they are sometimes called prepolymers. The two terms can be used interchangeably to refer to acrylic compounds entering the invention system, since the context would always clarify the presentation.

The residual initiator in the prepolymer of the second component is the intrinsic initiator concentration remaining in the product after synthesis. Indeed, the prepolymer is obtained by condensation of a monomer, using an initiator; it is eliminated by being more or less pushed to the end of the process. According to the invention, the residual initiator in the prepolymer is less than 0.1%, but in an optimum manner, it is less than 0.05% and is ideally zero. The assay is performed by standard techniques, for example by potentiometry, giving excellent precision.

According to an advantageous feature of the invention system, the second component comprises said acrylic polymer dissolved in said monomer in an amount adequate to form a gel with viscosity of 0.02 Pa·s to 500 Pa·s. Preferably, the viscosity of the gel obtained is between 0.1 Pa and 10 Pa·s. The polymerization kinetics of acrylic compounds are well known to those skilled in the craft; certain tests are sufficient to determine, for certain compounds, the proportions to implement to achieve the desired viscosity.

According to another advantageous feature of the invention system, the second component includes between 1% to 20% acrylic polymer by weight, preferably between 5% and 15%. Note that these levels are particularly low compared with the acrylic gels described in the literature, which contain at least 40% of PMMA and generally between 45% and 50% or 60% of PMMA.

A particularly advantageous characteristic of the invention system is that the residual initiator in the second component is less than 0.02%, preferably less than 0.005%. Ideally, the residual initiator is zero.

This very-low or non-existent contribution of initiator in the gel derived partially from a choice of a polymer itself containing little or no initiator, but also because a small proportion of polymer is added to the second component. The combination of these two characteristics is crucial to optimize the result. Indeed, it was observed that even when using a polymer with the specification indicating that it is devoid of initiator, polymerization occurs early in the gel, suggesting that the polymer still contains a fraction of trace amounts of initiator, not detectable despite the sensitivity of the assay methods, but still enough to induce a reaction.

In a preferred embodiment of the invention system, the acrylic polymer of the second component is selected from polymethylmethacrylate (PMMA) polymers or polymethylmethacrylate copolymers.

Also preferably, in the invention system, the monomer is selected from methyl methacrylate (MMA), butyl methacrylate, triethylene glycol dimethacrylate (TEGDMA), urethane dimethacrylate (UDMA), or [bis-glycidyl] methacrylate (bis-GMA).

According to the invention, the activator may be a tertiary amine, preferably the dimethyl (DMPT), and the inhibitor may be hydroquinone (HQ). The latter plays a stabilizing role in the second component by inhibiting free radical polymerization reactions between monomer and polymer, which eventually occur spontaneously even in the absence of initiator.

In this case, the second component may comprise between 0.1% and 3% dimethyl, and 1 ppm to 100 ppm of hydroquinone, preferably using between 0.5% and 2.5% dimethyl, and preferably also 20 ppm to 75 ppm hydroquinone. The man of the art knows how to choose the appropriate quantities of these reagents commonly implemented for the intended application.

Regarding the first component of the invention system, it can be formulated in a conventional manner or according to original principles, so as to provide an acrylic polymer which reacts with the second component to form curable bone cement.

Thus, according to the invention, in the first component the acrylic polymer may be chosen from polymethylmethacrylate (PMMA) polymers or polymethylmethacrylate copolymers. This polymer, which is usually, but not necessarily, different from the acrylic polymer used in the second component, can be chosen without difficulty by those skilled in the craft, both regarding its nature and its molecular weight. It may be in the usual form of a dry powder, but also in the form of a gel.

It may contain higher or lower residual amounts a polymerization initiator; this parameter is unimportant here because these add up to the amount of initiator can be added to the powder state in the first component for a rapid response when mixed with the second component. When making a bone cement powder, the man of the art takes into account the initiator quantities of the polymer (prepolymer beads themselves can contain up to 5% by mass) to calculate the quantity to add in the first component to get the total amount due. Sometimes it is not necessary to add the initiator powder form because it is provided in sufficient quantity by the prepolymer.

Thus, the first component contains an initiator, which may be a peroxide, preferably benzoyl peroxide (BPo). In this case, the first component may preferably have 0.1% to 3% total benzoyl peroxide. The low values of this interval (i.e. 0.5% to 0.1%) are particularly interesting because they may increase the injection time, thanks to the small amount of BPo in the first component, related to giving preference to a low DMPT content (less than 1%) in the second component.

The first component of the invention system may also include, commonly, an opacifier allowing visualization of the cement during its injection, and possibly also a calcium phosphate which acts as an opacifier and improves cement injectability.

According to another aspect of this invention, a composition is claimed as intended to form the second component of a system for preparing a bone cement polymer as described above, said composition comprising a monomer capable of dissolving an acrylic polymer, an activator polymerization and a polymerization inhibitor, said composition also comprising a biocompatible polymer dissolved in said acrylic monomer having an average molecular weight greater than 1,000,000 g/mol and a residual content of less than 0.1% initiator, to form a gel of determined viscosity.

The composition of the invention advantageously comprises said acrylic polymer dissolved in said monomer in an amount adequate to form a gel with viscosity of 0.02 Pa·s to 500 Pa·s, preferably between 0.1 and 10 Pa·s Pa.

Interestingly, the composition of the invention comprises 1% to 20% of acrylic polymer by weight. Preferably, the composition constituting the second component comprises between 5% and 15% of acrylic polymer by weight.

According to an advantageous characteristic, the composition of the invention has a residual initiator is less than 0.02%. Particularly preferably, it is less than 0.005%.

According to the invention, the monomer may be selected from methyl methacrylate (MMA), butyl methacrylate, triethylene glycol dimethacrylate (TEGDMA), urethane dimethacrylate (UDMA), or [bis-glycidyl] methacrylate (bis-GMA) and the acrylic polymer is selected from polymethylmethacrylate polymers or polymethylmethacrylate copolymers.

In a preferred embodiment, the composition of the invention comprises between 0.1% and 3% dimethyl (DMPT), preferably between 0.5% and 2.5%, and 1 ppm to 100 ppm Hydroquinone (HQ), preferably between 20 ppm and 75 ppm. These levels correspond to common values for the reactants involved, which the man of the art can therefore implement without particular difficulty to embody the invention.

When the first and second components of the invention system are combined, the cement obtained after homogeneous mixture is immediately ready for use. Indeed, mixing the first component of the gel resulted in less than two minutes to obtain a cement whose viscosity level is between 40 Pa and 100 Pa, i.e., an ideal viscosity for enabling both starting cement injection with a reduced risk of leaks into the circulatory system or surrounding tissues, and maintaining a maximum response time before setting. The waiting time is cut. The waiting time is defined as the time required for the viscosity to reach 40 Pa, from the start of mixing the two components.

The injection time is defined as the time required to move to cement a viscosity from 40 Pa·s (or its original viscosity when it is higher) to 1,500 Pa s [Boger et al. Eur. Spine J., Vol. 18, 2009].

Thus, this invention relates to the application of a two-component system or a composition as described above for the manufacture of acrylic cement with initial viscosity between 40 Pa·s to 100 Pa·s within two minutes from the contact of these components.

The removal of the waiting time, which can reach up to 15 minutes for cements called "low-viscosity", is an advantage for surgical teams. It was also observed, unexpectedly, and with particular interest, that the invention system provides a broader window of time during which the cement is injectable. The use of an alternative to the liquid gel usually used in surgical acrylic cement can thus increase the injection time of cement.

According to the objective and contrary to the prior state of the art, the composition of this invention is stable at normal temperature, which allows its transport and storage without refrigeration constraints. Its long-term stability is made possible by the use of a low content of polymer initiator (<0.1%) and average molecular weight greater than 1,000,000 g/mol. Because of this high molecular weight, it becomes possible to obtain a stable gel with required viscosity, with a lesser amount of prepolymer dissolved in the monomer (powder/liquid ratio <0.2). This reduced amount of dissolved polymer provides a small amount of residual initiator; it is easy to stabilize through the use of hydroquinone type inhibitor.

In contrast, in compositions for bone cements in gel form known in the prior state of the art, the gel is obtained by dissolving a polymer of average molecular weight, i.e. 10,000 g/mol at 500,000 g/mol. Obtaining a viscous consistency requires the addition of a high proportion of polymers, 30% to 70% by weight. Although the residual BPo content of this polymer is low (which is never specified), this additional material involves the introduction of residual initiator in significant amounts, which necessarily leads to disruption of the stability of the gel in medium term, even in the presence of a reagent stabilizer.

The cements thus obtained can be advantageously implemented in many ways, following the indication and surgical technique used. The claimed application of a system according to the invention described above or a composition is also described for the manufacture of acrylic cement for use in orthopedics and dentistry and especially in vertebroplasty, kyphoplasty or vertebroplasty.

BRIEF DESCRIPTION OF THE DRAWING FIGURES

This invention will be better understood, and relevant details will appear, thanks to the description which will be made of one of its variants, in conjunction with the accompanying figures in which.

DETAILED DESCRIPTION

EXAMPLE 1

Figure 1:
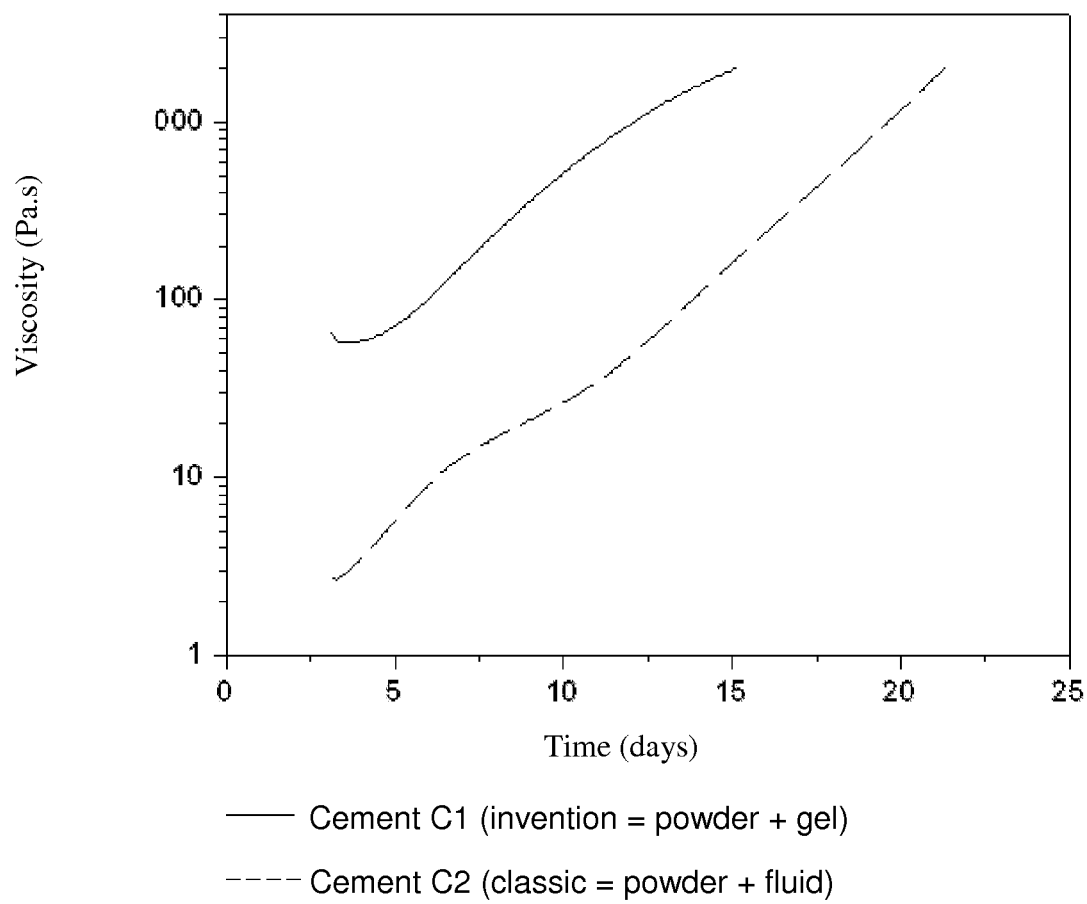
FIG. 1 shows the comparative evolution of the viscosity of a conventional cement and the cement of the invention.

System for Preparing a Bone Cement According to the Invention

The first component of the system is formulated as follows (in weight contents):
PMMA 49.5%
Total BPo 0.5%
Zirconium oxide 45%
Hydroxyapatite 5%

A mixture of two grades of PMMA is used. Their molecular weight is respectively 400,000 g/mol and 200,000 g/mol, and their residual BPo 0.4% and 5%. The total BPo is provided by both the prepolymer and powder BPo added. A dry powder is obtained, which is a mixture of PMMA beads and other powder ingredients.

The second component is formulated as follows (in weight contents):
MMA 94%
PMMA 5%
DMPT 1%
HQ 20 ppm The PMMA used has a molar mass of 1,500,000 g/mol and is free of residual BPo.

The residual BPo is measured by a standard technique of potentiometry. PMMA is dissolved to release its BPo. BPo solution reacts with iodide ions to form iodine, $I_2$, which in turn is determined by sodium thiosulfate. The method provides an assay with a precision of at least 0.01%.

Preparation of the Gel:

The masses of MMA, DMPT and HQ are added to an Erlenmeyer flask, which is placed under stirring until well blended (about 2 minutes). The prepolymer powder (PMMA) is added and the mixture is stirred until complete dissolution of the particles, generally overnight. The dissolution time depends on the average molecular weight of PMMA and particle size (it increases with the molar mass and particle diameter).

This gives a clear translucent gel with 0.1 Pa·s viscosity. The residual BPo content in the gel is zero (or near zero, if BPo remained in non-detectable trace).

A cement is prepared by mixing the two components up to 27.2 g of powder and 10.0 g of gel.

The powder, gel and all materials necessary to the mixture are conditioned at 20° C. and 45% relative humidity in a climatic chamber at least 12 hours before creating the powder/gel blends. The powder is placed in a bowl made of polyethylene and the gel is poured on the powder. The stopwatch is started immediately ($t=t_0$). The mixture is kneaded with a spatula until the polyethylene is homogenized. The mixing time is between 30 seconds and one minute. The paste is then placed in a "double gap" type rheometer in which the cement is subjected to dynamic shear. The room where the rheometer is found is also regulated at 20° C. The rheometer and the data acquisition system measures are initiated as early as possible (in practice at $t=t_0+3$ minutes).

The measured initial viscosity of C1 cement is 60 Pa·s

EXAMPLE 2

Comparative Evolution of the Viscosity of a Conventional Cement and a Cement According to the Invention The cement prepared according to Example 1 (C1) is compared to a C2 cement, prepared from a first component same as above, and a second component expressed as follows (in weight contents):
MMA 99%
DMPT 1%
HQ 20 ppm
This gives a fluid viscosity of approximately 0.01 Pa.

A C2 cement is prepared by mixing the two components to the tune of 27.2 g of powder and 9.2 g of liquid.

It is noted that the total amounts of prepolymer and monomer made by the two components have been established so that the polymer/monomer ratio is maintained between the two cements. This ratio is 1.6 for C1 as for C2.

Both C1 and C2 cements are prepared using the protocol described in Example 1. The evolution of the viscosity is recorded as a function of time. The measurement is stopped when the viscosity is greater than 1,500 Pa·s. FIG. 1 shows the measurement results.

These results demonstrate that the initial viscosity of C1 cement according to the invention is much higher than that of conventional C2 cement (about 2 Pa·s for C2 and 60 Pa·s for C1). C1 cement is initially at a viscosity sufficient to start the injection, while the C2 cement reaches the viscosity of 40 Pa·s at the end of 12.5 minutes (waiting time).

C1 cement then takes more than 12 minutes to reach the viscosity of 1500 Pa·s, while the C2 cement arrived there in 9.2 minutes. The use of the invention system therefore represents a significant gain of available injection time.

EXAMPLE 3

Stability of the Gel During its Preservation

The stability of two gels during their preservation and storage was studied. G1 gel is prepared according to the invention, while G2 gel is formulated with a classic recipe. The formulations can obtain two gels with very similar initial viscosity, the evolution of which can be compared. The values are the weight contents.
G1 Gel:
MMA 94%
PMMA 5%
DMPT 1%
HQ 20 ppm
The PMMA used has a molar mass of 1,500,000 g/mol and it is completely free of residual BPo. The gel obtained has a content of 0% BPo, and its viscosity rises to 0.2 Pa·s.
G2 gel:
MMA
PMMA 20%
DMPT 1%
HQ 20 ppm The PMMA used has a molecular weight of 450,000 g/mol and a residual BPo content less than 0.8%. The gel obtained has a content of 0.2% BPo and its viscosity is 1 Pa s The gels are prepared using the protocol outlined in Example 1. The evolution in time of the viscosity of two gels is determined. The test conducted is an accelerated aging test in which the gels were kept at a temperature of 60° C. until final curing. At this temperature, the equation, giving the number of days simulated Y with the number of days in the oven X is:

$$Y=13X$$

Thus, for a test conducted over 14 days, the simulated aging corresponds to a period of 182 days.

Procedure

The same procedure is followed for both gels. Once the gel was obtained, a first sample (about 3 ml) was collected and its viscosity was measured at 20° C. This is the reference viscosity. Then, the Erlenmeyer flask is stoppered, and the rest of the gel is placed in an oven at 60° C. to accelerate the natural aging of the product. Then, a sample of 3 ml of gel is taken daily, its temperature is reduced to 20° C. and a new viscosity measurement is carried out at 20° C.

Figure 2:
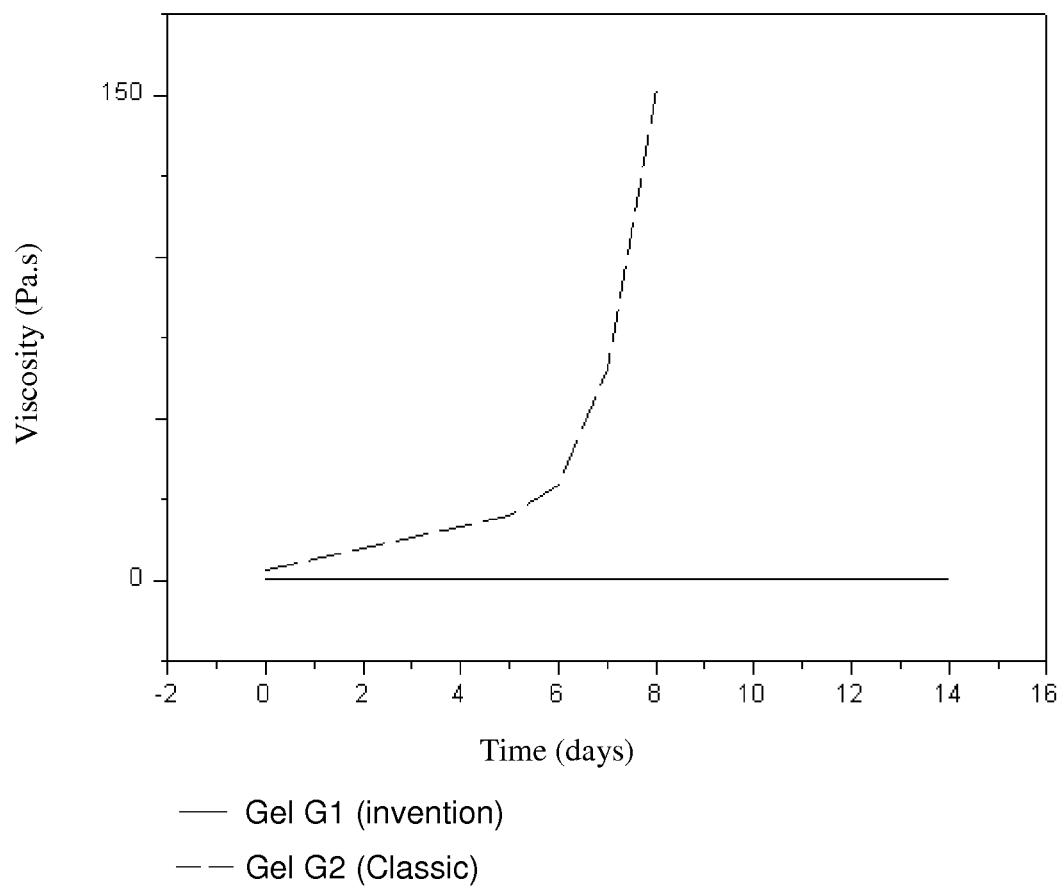
FIG. 2 shows a stability test comparison of two gels designed to form the second component of a system according to the invention, one conventional and the other according to the invention.

FIG. 2 shows the evolution over time of the viscosity of the two gels. The test was conducted for 14 days, simulating 6 months of aging.

The comparative evolution of viscosity versus time between the two G1 and G2 gels indicates the relative stability of the two products.

The viscosity of the G2 gel increases progressively during the first days of aging until the total curing of the product (hardening) at 8 days, i.e. 3.5 actual simulated months. The G1 gel of the invention has a viscosity much more stable over time, since its viscosity level remains unchanged after 14 days of aging at 60° C., which corresponds to a real aging duration of 6 months.

The comparison between the two sets of measurements shows that the G1 gel according to this invention is much more stable than that based on the prior state of the art. The G1 gel may be transported and stored at ambient conditions without risk of premature polymerization.

What is claimed is:
1. A system for the preparation of a polymer bone cement, consisting of two components reacting with each other when they are mixed to form a solid polymer material,
wherein the first component consists of
a biocompatible acrylic polymer, and
an initiator capable of initiating a polymerization reaction, and
the second component consists of
an acrylic monomer,
a polymerization activator,
a polymerization inhibitor, and
a biocompatible acrylic polymer dissolved in said acrylic monomer, identical or different from the polymer of the first component, having an average molecular weight greater than 1,000,000 g/mol and a residual initiator less than 0.1%, to form a gel of determined viscosity.

2. The system according to claim 1, wherein the second component includes said biocompatible acrylic polymer dissolved in said monomer in an adequate amount to form a gel of determined viscosity ranging from 0.02 Pas to 500 Pas.

3. The system according to claim 1, wherein the second component includes between 1% and 20% of said biocompatible acrylic polymer by weight.

4. The system according to claim 1, wherein the residual initiator in the second component is less than 0.02%.

5. The system according to claim 1, wherein in the second component, said biocompatible acrylic polymer is selected from acrylic polymethylmethacrylate polymers or polymethylmethacrylate copolymers.

6. The system according to claim 1, wherein the acrylic monomer is selected from methyl methacrylate, butyl methacrylate, butyl methacrylate, triethylene glycol dimethacrylate, urethane dimethacrylate, or bis-glycidyl methacrylate.

7. The system according to claim 1, wherein the activator is a tertiary amine, and the inhibitor is hydroquinone.

8. The system according to claim 1, wherein the second component includes between 0.1% and 3% of N,N-dimethyl-para-toluidine, and 1 ppm to 100 ppm hydroquinone.

9. The system according to claim 1, wherein the first component, the biocompatible acrylic polymer is selected from polymethylmethacrylate polymers or polymethylmethacrylate copolymers.

10. The system according to claim 1, wherein the initiator is a peroxide.

11. The system according to claim 1, wherein the first component includes between 0.1% and 3% total benzoyl peroxide.

12. A system for the preparation of a polymer bone cement, consisting of two components reacting with each other when they are mixed to form a solid polymer material,
wherein the first component consists of
a biocompatible acrylic polymer, and
an initiator capable of initiating a polymerization reaction,
an opacifier, and
calcium phosphate, and
the second component consists of
an acrylic monomer,
a polymerization activator,
a polymerization inhibitor, and
a biocompatible polymer dissolved in said acrylic monomer, identical or different from the polymer of the first component, having an average molecular weight greater than 1,000,000 g/mol and a residual initiator less than 0.1%, to form a gel of determined viscosity.

13. A method for manufacturing acrylic cement, comprising:
combining the first component and the second component of claim 1, wherein an initial viscosity is between 40 Pas and 100 Pas within two minutes from contact of the first and second components.

14. The method according to claim 13, further comprising:
utilizing the acrylic cement in orthopedics, dentistry cementoplasty, vertebroplasty or kyphoplasty.

15. The composition according to claim 2, wherein the determined viscosity ranges from 0.1 Pas to 10 Pas.

16. The composition according to claim 1, wherein the second component includes between 5% and 15% of the biocompatible acrylic polymer by weight.

17. The composition according to claim 1, wherein the residual initiator in the second component is less than 0.005%.

18. The system according to claim 1, wherein the second component includes 0.5% to 2.5% of dimethyl, and 20 ppm to 75 ppm hydroquinone.

19. The system according to claim 1, wherein the initiator is benzoyl peroxide.

20. A system for the preparation of a polymer bone cement, consisting of:
a first component that consists of biocompatible polymethylmethacrylate, benzoyl peroxide, zirconium oxide and hydroxypatite; and
a second component that consists of a gel which includes biocompatible polymethylmethacrylate dissolved in methylmethacrylate monomer, N,N-dimethyl-para-toluidine and hydroquinone, the polymethylmethacrylate of the second component having an average molecular weight greater than 1,000,000 g/mol and is free from residual benzoyl peroxide,
wherein an initial viscosity is between 40 Pas and 100 Pas within two minutes from contact of the first and second components.

* * * * *